（12）United States Patent
Muller et al.

(10) Patent No.: US 11,672,445 B2
(45) Date of Patent: Jun. 13, 2023

(54) INJECTOR FOR TRANSCUTANEOUSLY INTRODUCING A SENSOR INTO A PATIENT

(71) Applicant: EyeSense GmbH, Grossostheim (DE)

(72) Inventors: Achim Muller, Grossostheim (DE); Tom Meissner-Braun, Uberlingen (DE); Matthias Pischan, Darmstadt (DE)

(73) Assignee: EyeSense GmbH, Grossostheim (DE)

( * ) Notice: Subject to any disclaimer, the term of this patent is extended or adjusted under 35 U.S.C. 154(b) by 1010 days.

(21) Appl. No.: 16/253,649

(22) Filed: Jan. 22, 2019

(65) Prior Publication Data
US 2019/0223768 A1    Jul. 25, 2019

(30) Foreign Application Priority Data

Jan. 22, 2018   (DE) .......................... 102018101283.7

(51) Int. Cl.
*A61B 5/145*   (2006.01)
*A61B 17/34*   (2006.01)
(Continued)

(52) U.S. Cl.
CPC ...... *A61B 5/14503* (2013.01); *A61B 5/14532* (2013.01); *A61B 5/6848* (2013.01); *A61B 17/3421* (2013.01); *A61B 17/3468* (2013.01); *A61B 5/0031* (2013.01); *A61B 5/14507* (2013.01); *A61B 5/14546* (2013.01); *A61B 5/683* (2013.01); *A61B 2017/3409* (2013.01);
(Continued)

(58) Field of Classification Search
CPC .......... A61B 5/14532; A61B 2560/063; A61B 5/14503; A61B 5/6849; A61B 2017/3407; A61B 2017/347
See application file for complete search history.

(56) References Cited

U.S. PATENT DOCUMENTS 7,381,184 B2   6/2008   Funderburk et al.
3,029,442 A1   10/2011  Funderburk et al.
(Continued)

FOREIGN PATENT DOCUMENTS

CN    106137214    11/2016
JP    2015509011   3/2015
(Continued)

*Primary Examiner* — Christian Jang
*Assistant Examiner* — Karen E Toth
(74) *Attorney, Agent, or Firm* — Volpe Koenig

(57) ABSTRACT

An injector for transcutaneously introducing a sensor into a patient, including a cannula, a base element, a sliding element arranged displaceably on the base element, for transcutaneously introducing the cannula into the patient in an injection direction, and including an ejection element for automatically pulling the cannula out of the patient counter to the injection direction by the ejection element in an ejection operation. The injector has a locking element for the ejection element such that, in a delivery state, the ejection element is lockable in an energy-charged state, and the sliding element and the locking element are configured to interact indirectly or directly in order, in an injection state, when the cannula is introduced transcutaneously into the patient, to release the locking of the ejection element in order automatically to start the ejection operation.

13 Claims, 12 Drawing Sheets

(51) Int. Cl.
*A61B 5/00* (2006.01)
*A61B 90/00* (2016.01)

(52) U.S. Cl.
CPC ... *A61B 2090/034* (2016.02); *A61B 2090/035* (2016.02); *A61B 2560/045* (2013.01); *A61B 2560/0425* (2013.01); *A61B 2560/063* (2013.01); *A61B 2560/066* (2013.01); *A61M 2205/3507* (2013.01); *A61M 2230/201* (2013.01)

(56) References Cited

U.S. PATENT DOCUMENTS

| | | | |
|---|---|---|---|
| 8,465,448 | B2 | 6/2013 | Garcia De Castro Andrews |
| 9,931,066 | B2 | 4/2018 | Pace et al. |
| 2004/0133164 | A1 | 7/2004 | Funderburk et al. |
| 2008/0249466 | A1 | 10/2008 | Aubert et al. |
| 2010/0004597 | A1* | 1/2010 | Gyrn .................... A61M 5/158 |
| | | | 604/138 |
| 2010/0217105 | A1 | 8/2010 | Yodfat et al. |
| 2011/0040245 | A1* | 2/2011 | Garcia De Castro Andrews ........ |
| | | | A61M 37/0069 |
| | | | 604/60 |
| 2012/0123324 | A1 | 5/2012 | Schmalz |
| 2013/0150691 | A1* | 6/2013 | Pace .................... A61B 5/1451 |
| | | | 600/347 |
| 2016/0243302 | A1 | 8/2016 | Gyrn |
| 2017/0028128 | A1 | 2/2017 | Cole et al. |
| 2017/0303831 | A1 | 10/2017 | Tsubouchi et al. |
| 2018/0235520 | A1* | 8/2018 | Rao .................... A61B 5/14503 |
| 2019/0223769 | A1 | 7/2019 | Muller et al. |

FOREIGN PATENT DOCUMENTS

| | | |
|---|---|---|
| JP | 2016128031 | 7/2016 |
| WO | 2006092317 | 9/2006 |
| WO | 2016120920 | 8/2016 |
| WO | 2016128334 | 8/2016 |

* cited by examiner

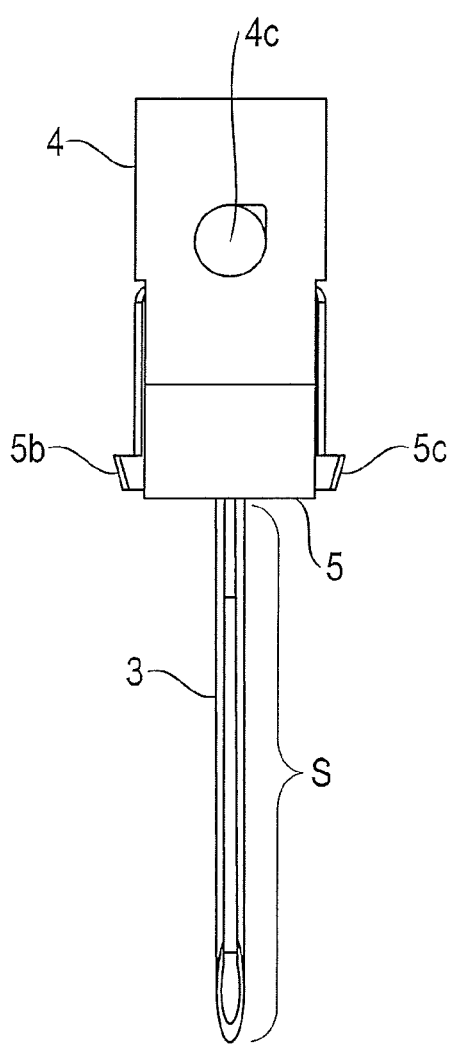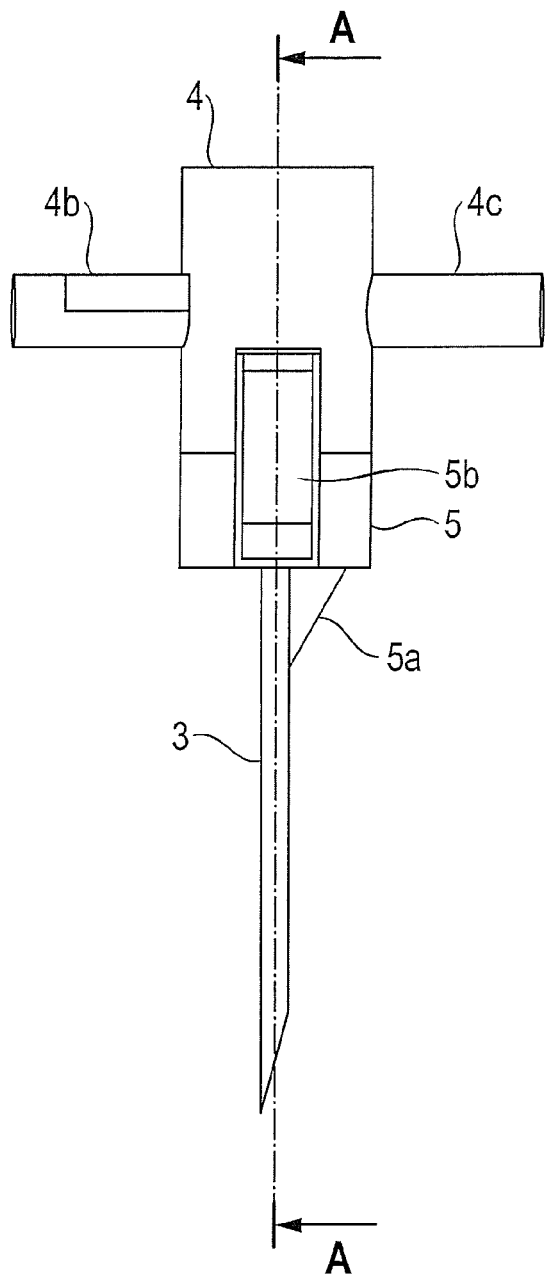
Fig. 2A
Fig. 2B

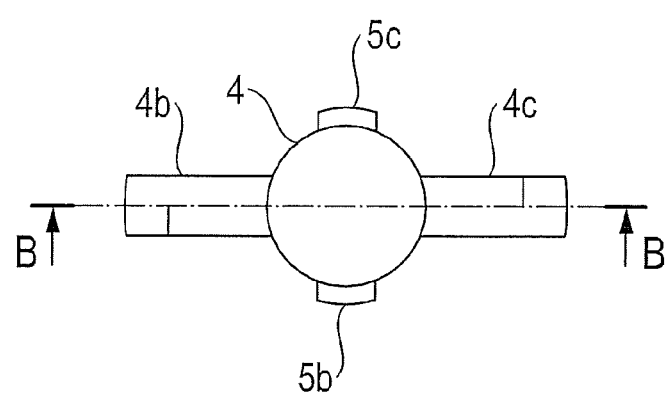
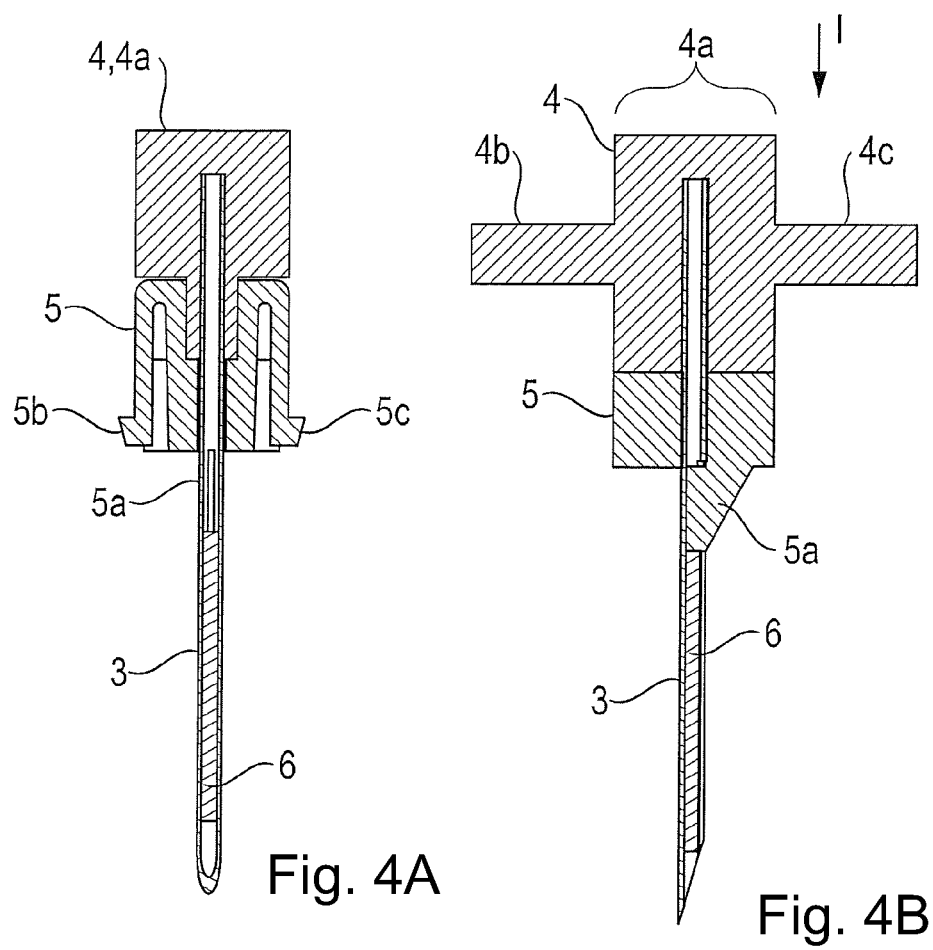
Fig. 3
Fig. 4A
Fig. 4B

INJECTOR FOR TRANSCUTANEOUSLY INTRODUCING A SENSOR INTO A PATIENT

INCORPORATION BY REFERENCE

The following documents are incorporated herein by reference as if fully set forth: German Patent Application No. 10 2018 101 283.7, filed Jan. 22, 2018.

BACKGROUND

The invention relates to an injector for transcutaneously introducing a sensor into a patient. The introducing of a sensor into a patient is necessary for diverse medical applications, in particular in order to obtain readings from the patient, such as, for example, glucose values or lactose values.

U.S. Pat. No. 8,029,442 B2 discloses an injector for transcutaneously introducing a sensor into a patient, in which a slotted cannula and a sensor located therein are introduced transcutaneously into a patient by a sliding element. After the injection operation is finished, the cannula is pulled out of the patient again by an ejection spring.

SUMMARY

The present invention is based on the object of providing an injector for transcutaneously introducing a sensor into a patient, said injector increasing the safety during the injection operation and increasing the use comfort for the user.

This object is achieved by an injector having one or more features of the invention. Advantageous refinements are claimed in the dependent claims.

The injector according to the invention for transcutaneously introducing a sensor into a patient has a cannula, a base element, a sliding element arranged displaceably on the base element, for transcutaneously introducing the cannula into the patient in an injection direction, and an ejection element for automatically pulling the cannula out of the patient counter to the injection direction by the ejection element in an ejection operation.

It is essential that the injector has a locking element for the ejection element such that, in a delivery state, the ejection element is lockable in an energy-charged state, and the sliding element and locking element are designed so as to interact indirectly or directly in order, in an injection state, when the cannula is introduced transcutaneously into the patient, to release the locking of the ejection element in order automatically to start the ejection operation.

The injector according to the invention therefore enables automatic starting of the ejection operation after the injection operation is finished.

Furthermore, the energy required for the ejection, i.e. for pulling the cannula out of the patient, is provided by the ejection element. The ejection element is thereby locked in an energy-charged state in a delivery state. The sliding element and locking element are designed so as to interact such that, in the injection state, when the cannula is introduced transcutaneously into the patient, the locking element is releasable, and therefore the ejection, i.e. the pulling out of the needle, takes place automatically using the energy stored in the ejection element.

The injector has the advantage that the ejection operation does not have to be carried out manually by the user. By this means, in particular no grasping or a manual change in direction after the end of the injection operation is necessary, and therefore impacts or a displacement of the injector, which may lead to causing pain to the patient, to erroneous placing of the sensor or to maladjustment of the injector, are avoided. Furthermore, the energy necessary for the ejection operation is predetermined by the ejection element energy stored in the delivery state. It is therefore not necessary for, for example, the user during a manual injection operation to simultaneously provide the energy for an ejection operation, for example by compressing a spring. The pressure to be exerted by the user during the injection operation is therefore not determined in the present invention by the energy or force necessary for the ejection operation, but rather can be coordinated with reliable carrying out of the injection operation. In particular, it is avoided in the present invention that, because of a high application of force, an injection operation—for example for tensioning an ejection spring—carries out tilting or displacement of the injector which may lead to unpleasantness for the patient or even to injury or erroneously introduced sensors.

The cannula is advantageously arranged in a distal end region on a cannula upper part of the injector. The cannula upper part is arranged on the base element so as to be displaceable in the injection direction, and the ejection element is designed so as to interact with the cannula upper part such that the cannula upper part is displaceable along the injection axis counter to the injection direction by means of the ejection element.

This results in a structurally simple refinement since both during the injection and during the ejection, the introduction of force into the cannula can take place via the cannula upper part and in particular a defined engagement surface is provided—indirectly or preferably directly—for the ejection element in order to conduct the force counter to the injection direction to the cannula via the cannula upper part in order to pull the cannula out of the patient.

The locking element is advantageously designed to be fixable on the base element in a fixing position and the cannula upper part is displaceable counter to the injection direction in an ejection position.

This results in a structurally simple refinement in which, in order to obtain the delivery state, the ejection element is brought into the energy-charged state and the locking element is subsequently arranged in the fixing position such that the energy of the ejection element remains stored. Furthermore, in this preferred embodiment, the injector is designed in such a manner that, in the injection state, the locking element is brought from the fixing position into the ejection position by the sliding element. In said ejection position, the locking element is now displaceable counter to the injection direction, and therefore, during the ejection operation, locking element, cannula and optionally cannula upper part are displaced counter to the injection direction by the energy stored in the ejection element, and therefore the cannula is pulled out of the patient.

It is advantageous here that the locking element is arranged on the base element so as to be rotatable, in particular so as to be rotatable about an injection axis, and is designed to be transferable from the fixing position into the ejection position by rotation of the locking element.

The injector is designed in such a manner that the cannula is introduced in an injection direction transcutaneously into the patient by the sliding element. This preferably takes place along a rectilinear injection axis. Said injection axis can lie obliquely with respect to the surface of the patient's tissue. It is particularly advantageous that the injection axis lies perpendicularly to the surface of the patient's tissue into which the sensor is intended to be introduced.

In the previously described advantageous embodiment, the locking element, as described above, is designed so as to be rotatable about the injection axis. This results in a structurally simple refinement since a displacement of the locking element takes place along the injection axis counter to the injection direction during the ejection operation and transfer of the locking element from the fixing position into the ejection position takes place by rotation about the injection axis. By this means, in a structurally simple refinement, the release of the locking element can take place, in particular by provision of bevels on sliding element and/or locking element, as explained in more detail below.

The locking element is advantageously arranged between the ejection element and the cannula upper part or at least engagement surfaces of the cannula upper part for the ejection element, such that a force can be transmitted in the ejection direction to the cannula upper part via the locking element by the ejection element.

In this advantageous refinement, a structural simplification therefore furthermore arises in that, firstly, the ejection element is locked in the fixing state by the locking element and, secondly, in the ejection state, the ejection element by an action of force on the locking element exerts an action of force for the ejection operation in a structurally simple manner, wherein the force is transmitted to the cannula upper part counter to the ejection direction via the locking element by the ejection element and is therefore transmitted to the cannula for pulling the cannula out of the patient.

The ejection element can be designed in a differing manner in order to store energy for the ejection operation. It lies within the scope of the invention to design the ejection element as a pressure accumulator in which a positive pressure or a negative pressure in relation to atmospheric pressure is stored. The locking element is designed in this case as a closure element for the ejection element designed as a pressure accumulator. In the fixing position, the locking element closes the pressure accumulator. In the ejection position, a discharge opening of the pressure accumulator that was previously closed by the locking element is opened. Pressure compensation by displacing the cannula, in particular displacing the cannula upper part, preferably the locking element, is achieved via pressure channels.

The ejection element is preferably in the form of a spring (ejection spring). This permits energy storage in a structurally simple manner by the spring being compressed or fixed in an extended state in the delivery state. The locking means is correspondingly designed in order, in the fixing position, to fix the spring in the compressed or extended state and, in the ejection position, said fixing is eliminated, and therefore an expansion or compression of the spring takes place, leading at least indirectly to the cannula being pulled out of the patient.

A particularly structurally simple advantageous refinement is produced by the spring being fixed in the compressed state, and therefore, in said delivery state, a force is present between base element and locking element which is arranged on the base element in the fixing position. In this case, the energy stored in the compressed spring is therefore available for the ejection. After the injection operation is finished, the locking means is transferred from the fixing position into the ejection position in which the spring is no longer fixed, and therefore expansion of the spring takes place, which is used for pulling the cannula out of the patient.

It is advantageous in particular here, as described previously, to design the locking element so as to be displaceable along the base element and in particular preferably to design the locking element to be rotatable about the injection axis in order to transfer the same from the fixing position into the ejection position.

A further structurally simple refinement is produced by the spring having a cylindrical construction, in particular with an oval, preferably circular cross section, and the center axis of the spring being arranged parallel to the injection axis, in particular by the cannula being arranged in the region of the center axis of the spring.

As previously described, the injector preferably has a cannula upper part on which the cannula is arranged with a distal end. In particular, it is advantageous for the sliding element and cannula upper part to be designed so as to interact in such a manner that, during the injection operation, the cannula upper part is displaceable in the injection direction by the sliding element. In this preferred embodiment, the action of force on the cannula therefore takes place indirectly by the user displacing the sliding element in the direction of the patient and an action of force thereby taking place on the cannula via the cannula upper part in order to insert the cannula transcutaneously into the patient.

The cannula is preferably connected fixedly, in particular preferably non-releasably, to the upper part. The cannula upper part advantageously surrounds the cannula at a distal end of the cannula.

The cannula upper part preferably has a central element and at least one guide extension. The base element preferably has at least one guide wall with a guide slot for the guide extension of the cannula upper part, for guiding the cannula upper part in the injection direction. In this advantageous refinement, the cannula is arranged on the central element. The sliding element advantageously engages on the guide extension, and therefore, when the sliding element is actuated, force is transmitted via the guide extension on the central element to the cannula. In particular, it is advantageous that the guide extension penetrates the guide wall of the base element and the sliding element is designed so as to engage on the guide extension on that side of the guide wall which faces away from the central element of the cannula upper part. This provides an effective guidance of the cannula upper part in the injection direction through the guide wall and the guide slot in the guide wall.

In an advantageous development, tilting of the cannula upper part during displacement in the injection direction is avoided by a respective guide extension being formed on two opposite sides on the cannula upper part and the base element correspondingly having at least two guide slots in the injection direction for the two guide extensions and the sliding element being designed so as to engage on both guide extensions.

The two guide slots can be formed here in a common guide wall of the base element. In particular, it is advantageous that the basic wall is designed in a manner surrounding the central element of the cannula upper part and preferably also the holding element. In particular, a guide wall in the form of a hollow cylinder is advantageous for a stable construction. It also lies within the scope of the invention that the base element has a plurality of guide walls for the cannula upper part and preferably for the holding element.

As described previously, the base element and/or the sliding element has at least one bevel, in particular a slotted guide, which is arranged in such a manner that, during the injection operation, rotation of the sliding element relative to the base element takes place in a proximal end region when the sliding element is displaced in the injection direction. By this means, rotation of the sliding element is obtained in a structurally simple manner when the cannula is completely or virtually completely introduced, in order to release the locking element and to start the ejection operation.

Sliding element and locking element therefore advantageously have corresponding contact surfaces which are arranged in such a manner that, by rotation of the sliding element, the locking element can be transferred from the fixing position into the ejection position. The locking element preferably has an extension and the sliding element a corresponding guide surface.

Base element and sliding element advantageously have corresponding guide elements which are designed and arranged in such a manner that the sliding element is rotatable relative to the base element only in the proximal end region. By this means, it is avoided that the user, before the proximal end region, already carries out a rotation of the sliding element relative to the base element, which could lead to a malfunction and in particular to a premature or non-materializing triggering of the ejection element.

For this purpose, a guide slot or a guide groove is advantageously formed on one of the two elements, base element and sliding element, and runs rectilinearly in the injection direction, but, in the proximal end region, reproduces the rotation of the sliding element relative to the base element. A guide extension is preferably formed on the other of the two elements, in particular a pin which engages in the aforementioned guide groove or the guide slot and/or penetrates same.

The sliding element preferably has one or more guide slots for the extension of the cannula upper part, said guide slots being arranged in such a manner that, after rotation of the sliding element into the proximal end region, the cannula upper part is displaceable counter to the injection direction. By this means, an ejection operation is possible in a structurally simple manner without the sliding element having to be moved counter to the injection direction.

In an advantageous refinement, during the ejection operation, displacement of the cannula upper part with cannula counter to the injection direction therefore takes place relative to the base element and relative to the sliding element, and therefore, during the ejection operation, no or at least a slight further displacement takes place between base element and sliding element.

The aforementioned bevel or oblique surface is preferably formed on the sliding element at a proximal end of the aforementioned guide slots. This results in a structurally simple construction.

The injector advantageously has a counterforce spring which is arranged between base element and sliding element in a manner acting counter to a displacement of the sliding element in the injection direction. This ensures that the injection operation is started only by pressure on the sliding element and, for example, does not already take place solely on the basis of the force of the weight of the sliding element. A further advantage of the present invention is shown here: said counterforce spring of the advantageous embodiment described here can be configured in a specific manner for generating a necessary counterforce which promotes a uniform, continuous displacement of the sliding element by the user. In particular, it is not necessary that, by compression of the counterforce spring during the injection, a sufficient counterforce for the ejection is formed at the same time by the counterforce spring. The counterforce spring will typically have a lower spring constant in relation to the ejection element and in particular in relation to an ejection element in the form of an ejection spring.

The injector according to the invention is preferably designed in accordance with DE102018101275.6.

BRIEF DESCRIPTION OF THE DRAWINGS

Further preferred features and embodiments will be explained below with reference to an exemplary embodiment and the figures, in which:

FIGS. 2A and 2B show side views of cannula, cannula upper part and holding element of the injector;

FIG. 3 shows a top view from above of the elements according to FIG. 2B;

FIGS. 4A and 4B show sectional illustrations of the elements from FIGS. 2A and 2B;

DETAILED DESCRIPTION

The same reference signs in the figures denote identical or identically acting elements.

Figure 1:
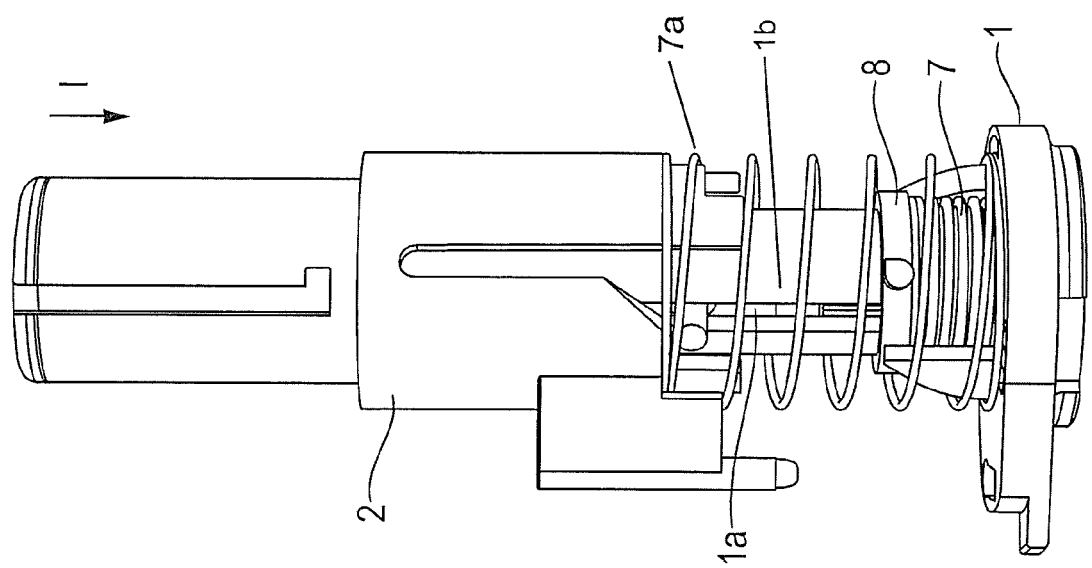
FIG. 1 shows a side view of an exemplary embodiment of an injector according to the invention for transcutaneously introducing a sensor into a patient.

FIG. 1 shows the exemplary embodiment of the injector according to the invention in a side view. The injector has a base element 1 and a sliding element 2. The sliding element is arranged on the base element so as to be displaceable in an injection direction I.

The injector can additionally have a housing which is arranged on the base element and surrounds the base element and the lower part, in particular the lower half of the sliding element 2 according to FIG. 1. For reasons of better representability, the housing is not shown in the figures.

In order to use the injector, a base plate is stuck onto the patient's skin and the injector is attached to the base plate by a bayonet closure formed on the lower side of the base element, and therefore the injector is arranged releasably on the base plate and therefore releasably on the patient. Similarly, the injector can already be attached to the base plate in the delivery state, and therefore injector and base plate are stuck onto the patient's skin.

In all of the figures, the patient's tissue is therefore located on the lower side, and therefore, in the figures, the lower regions show proximal regions and the upper regions show distal regions.

The base element has a region which is designed approximately as a hollow cylinder and which approximately surrounds a cannula 3 with a cannula upper part 4 and a holding element 5. These elements are illustrated separately in FIGS. 2A, 2B, 3, 4A, and 4B.

The cannula 3 is embedded at its distal end in a central element 4a (see FIG. 4B) of the cannula upper part 4 and connected fixedly thereto. The holding element 5 is arranged below the cannula upper part 4, said holding element 5 having, in the distal region, an indentation in which the cannula upper part 4 engages, wherein the holding element 5 is arranged on the cannula upper part 4 with a slight press fit.

The cannula upper part 4 furthermore has two extensions 4b, 4c which are arranged on opposite sides and extend perpendicularly to the longitudinal extent of the cannula 3 and therefore perpendicularly to the injection direction I.

FIG. 2A shows here a side view with a top view of the end side of the extension 4c, and FIG. 2B shows a side view with a longitudinal extent of the extensions 4b and 4c, the longitudinal extent lying in the plane of the drawing.

FIG. 3 shows a top view from above of the cannula upper part 4. FIG. 4A shows a section according to the intercepting line A-A in FIG. 2B, wherein the sectional plane lies perpendicularly to the plane of the drawing of FIG. 2A. FIG. 4B shows a section according to the intercepting line B-B in FIG. 3, wherein the sectional plane likewise lies perpendicularly to the plane of the drawing according to FIG. 3.

As is apparent, for example, in FIG. 2A, the cannula 3 has a slot in a proximal region S. FIG. 2A shows the top view from the front of the slot of the cannula 3. A sensor 6 is arranged in the cannula 3, as is apparent, for example, in FIGS. 4A and 4B.

Said sensor is intended to be inserted transcutaneously into the patient's tissue using the injector in order optically to determine readings by a detection element/detection unit designed as a detector. The basic principles of such an optical measurement are described in WO2016128334A1 and WO2006092317A1.

The insertion of other sensors, in particular sensors with electrodes for electrically sensing readings is likewise possible in a same manner.

As is apparent in particular in FIGS. 2B, 4A and 4B, the holding element 5 has a cam 5a which, in the region of the distal end of the sensor 6, engages in the cannula 3 through the slot therein and therefore lies against the upper distal end of the sensor 6 (see FIG. 4B).

The holding element 5 furthermore has fixing means 5b and 5c in the form of latching lugs, and therefore, at the end of an injection operation, the holding element 5 can be automatically locked on the base element.

Figure 5:
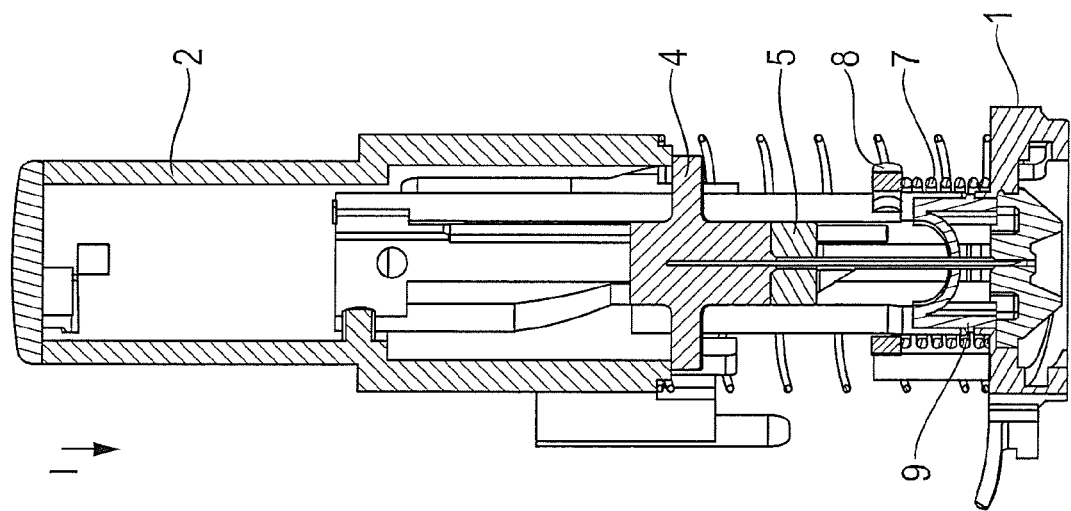
FIG. 5 shows a sectional illustration of the injector before the injection operation.

FIG. 5 shows a sectional illustration of the injector, wherein the sectional plane runs through the central axis of the cannula 3 and therefore through the injection axis. The state is illustrated prior to the injection operation, the state constituting the delivery state: the cannula and sensor are located within the injector, in particular within the base element 1.

Cannula 3 with sensor 6, holding element 5 and central element 4a of the cannula upper part 4 are arranged within a region of approximately cylindrical design of the base element 1. Said cylindrical region has guide slots which run rectilinearly in the injection direction I and of which a guide slot la is visible in FIG. 1.

The extensions 4b and 4c of the cannula upper part 4 penetrate the approximately cylindrical region of the base element 1. As is apparent in FIG. 5, the sliding element 2 acts on the extensions 4b and 4c outside the cylindrical region of the base element 1. The sliding element 2 is therefore guided displaceably in the injection direction on an outer wall of the cylindrical region of the base element 1, and central element 4a of the cannula upper part 4 and holding element 5 are guided displaceably in the injection direction on the inner side of the cylindrical region of the base element 1. The cylindrical region of the base element 1 therefore forms a guide wall 1b for said elements.

If the user now presses the sliding element 2 downwards in the injection direction, the force is transmitted via the extensions 4b and 4c to the central element 4a and therefore to the cannula 3. The force is also transmitted via the central element 4a to the holding element 5, and therefore said elements and also the sensor 6 are moved in the injection direction.

Figure 6:
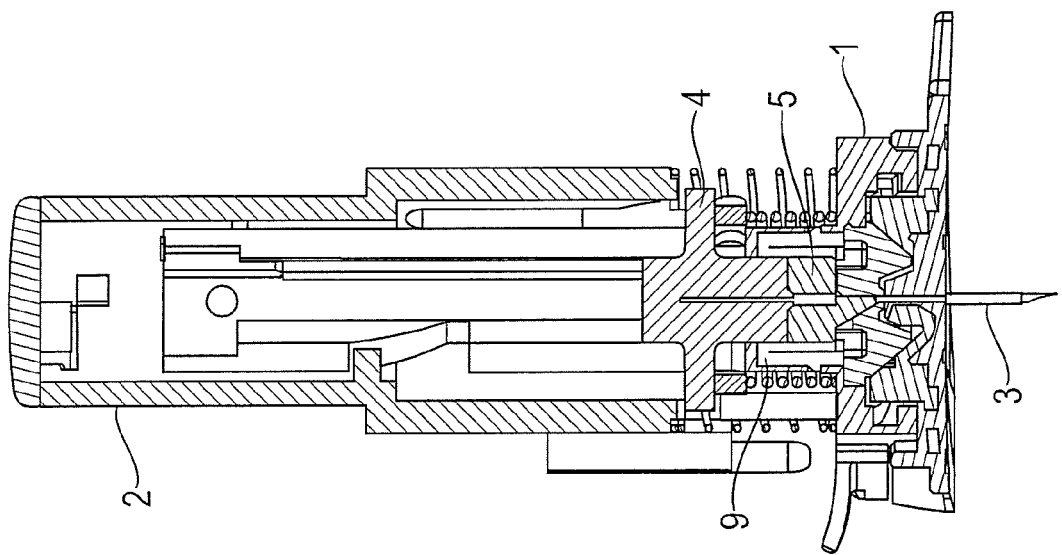
FIG. 6 shows a sectional illustration of the injector after the injection operation has ended.
Figure 7:
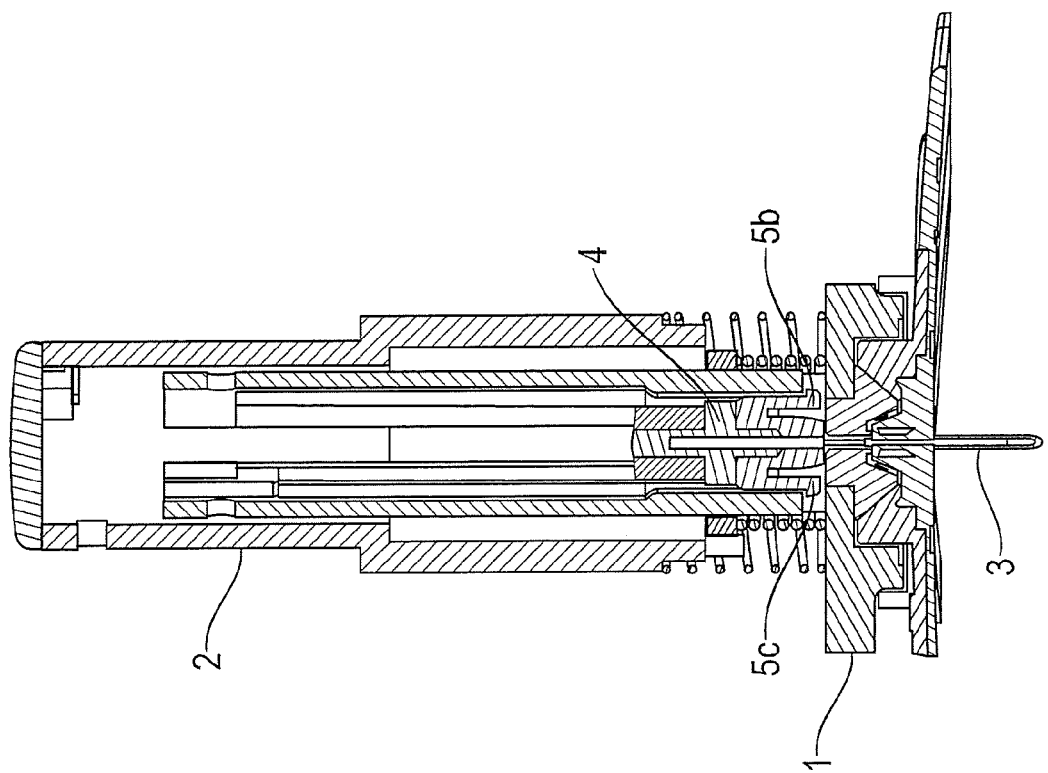
FIG. 7 shows a further sectional illustration at the end of the injection operation, wherein the sectional plane lies perpendicular to the sectional plane according to FIG. 6.

FIG. 6 shows the end of the injection operation: the sliding element 2 is completely pressed down, the cannula 3 with the sensor 6 has penetrated transcutaneously into the patient's tissue and the fixing means 5b and 5c in the form of latching lugs have latched into corresponding recesses of the base element 1, as is apparent in FIG. 7.

At the end of the injection operation, the holding element 5 is therefore automatically fixed to the base element 1.

During the subsequent ejection operation, the cannula upper part 4 is moved upward counter to the injection direction I, and therefore the cannula 3 is pulled out of the patient's tissue. Since, however, the holding element 5 is fixed to the base element 1, the holding element does not undertake said movement counter to the injection direction. A press fit which is possibly present between holding element 5 and cannula upper part 4 is overcome by the fixing using the latching lugs. Since the cam 5a of the holding element 5 continues to engage in the slot of the cannula 3 at the distal end of the sensor in the cannula, it is thereby prevented that, when the cannula 3 is pulled out, the sensor is also pulled out of the patient's tissue. In particular, an adhesion or rubbing between sensor and cannula can thereby also be overcome.

After the ejection operation is finished, the injector is removed from the previously mentioned base plate, and therefore only base plate and sensor 6 remain on the patient. Holding element 5 and sensor 5 are therefore designed as separate units.

The injector according to the present exemplary embodiment furthermore has an ejection element in the form of an ejection spring 7 and a locking element in the form of an ejection spring holding element 8 for the ejection element. As is apparent in FIG. 1, in the delivery state, the ejection spring 7 is arranged compressed between base element 1 and ejection spring holding element 8. The ejection spring 7 surrounds the cylindrical region of the base element 1 in a proximal region.

The ejection spring holding element 8 is of substantially annular design and has a pin both on the inner side and on the outer side. By use of the inner pin, the ejection spring holding element is fixed releasably to a guide of the base element running perpendicularly to the injection direction, see FIG. 8A. In the region marked by a circle in FIG. 8A, the inner pin of the ejection spring holding element 8 engages in a guide on the outer wall of the base element 1, and therefore no expansion of the ejection spring 7 is possible in this state. As explained in more detail below, sliding element 2 and ejection spring holding element 8 are designed so as to interact in such a manner that, at the end of the injection operation, rotation of the ejection spring holding element 8 takes place, and therefore the pin of the ejection spring holding element 8 is rotated to the left in the illustration according to FIG. 8A and thus enters the region of the guide slot 1a of the base element 1, and therefore expansion of the ejection spring 7 is possible.

Figure 8A:
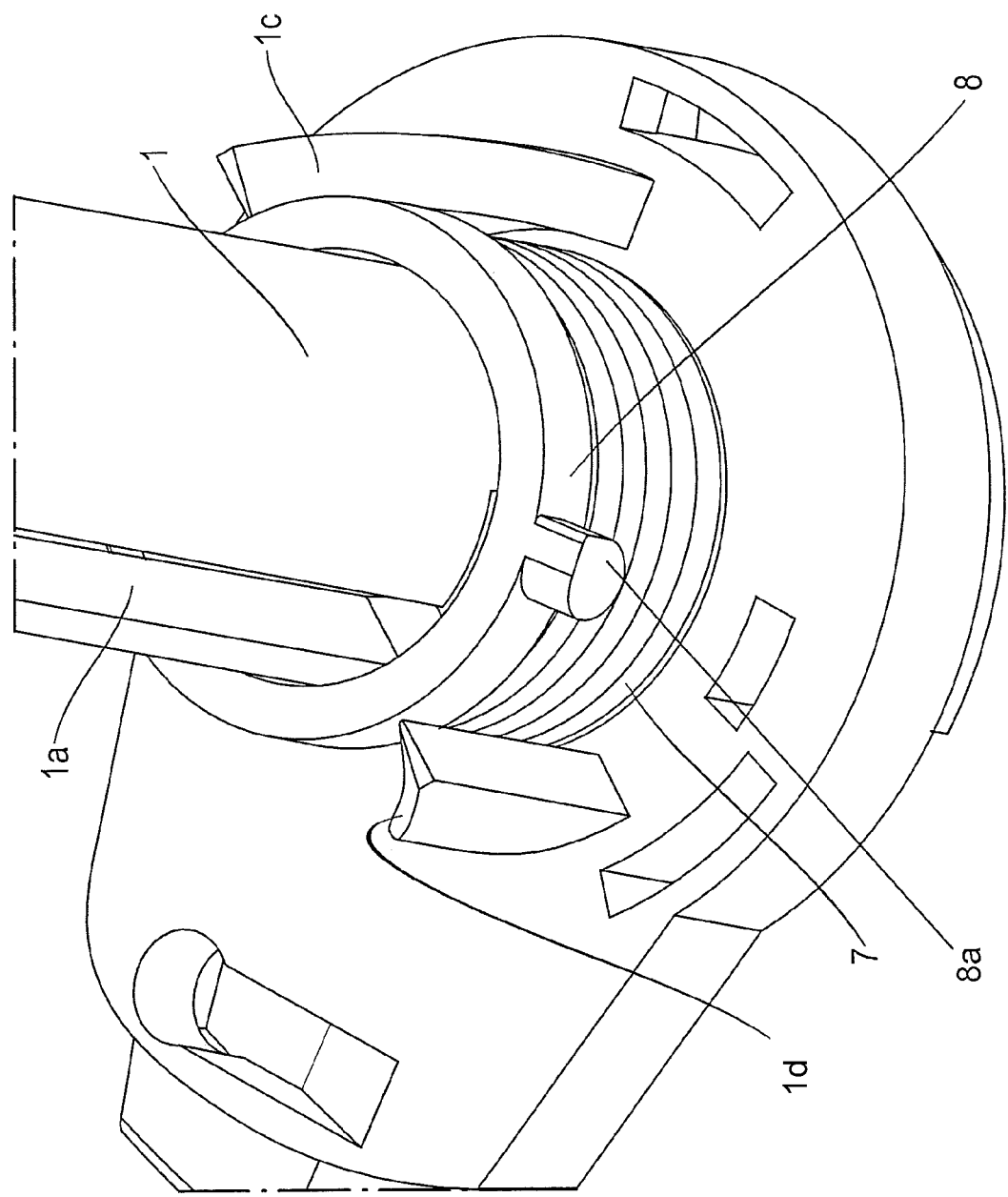
FIGS. 8A and 8B show detailed views of the detector with an ejection spring holding element.
Figure 8B:
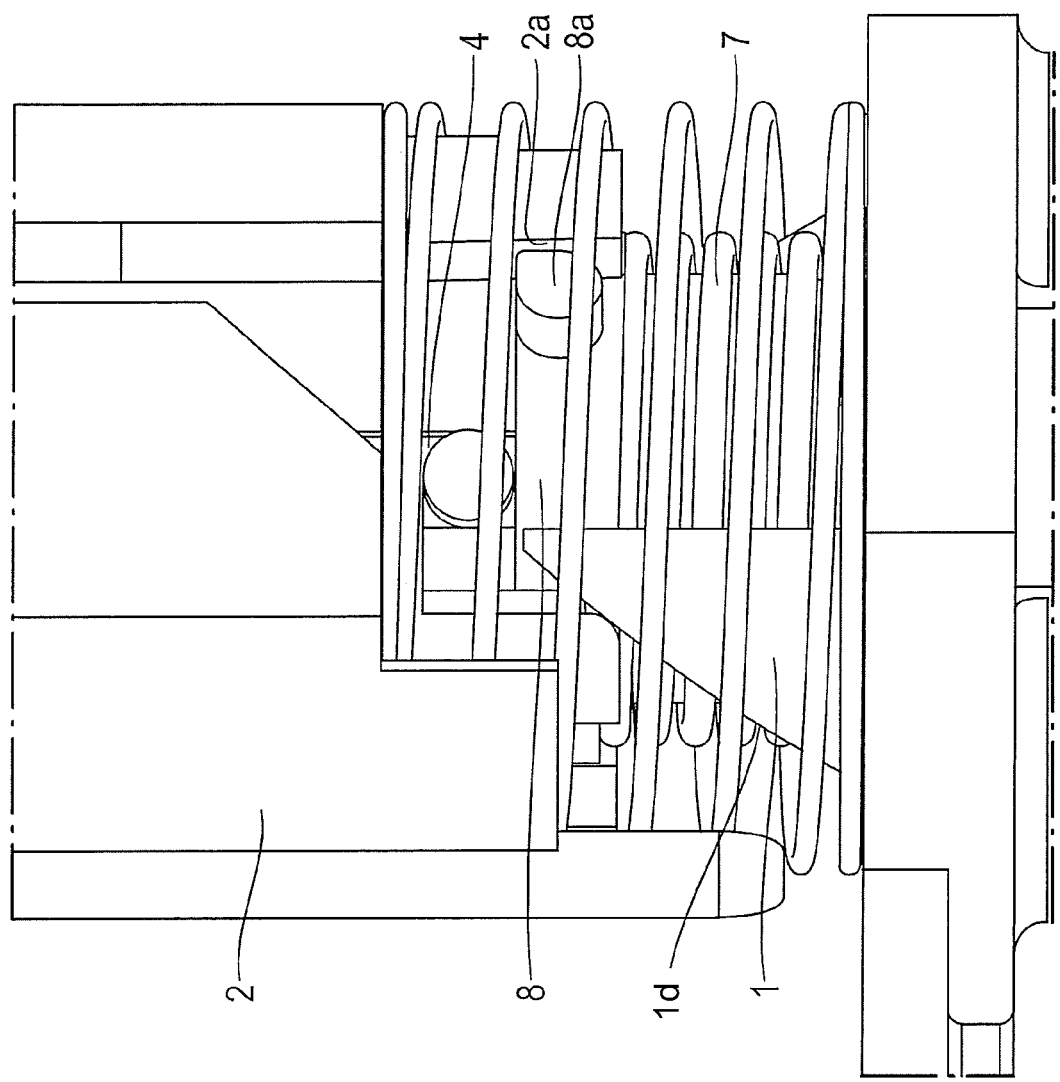

As is apparent in FIGS. 8A and 8B, the base element has, in a proximal region, two guides 1c and 1d which are designed as bevels, i.e. oblique surfaces, and enter into contact with corresponding contact surfaces of the sliding element 2 at the end of the injection operation. If the sliding element is pressed down further in said end region, rotation of the sliding element relative to the base element about the injection axis takes place because of the bevels 1c and 1d. For better clarification, elements, such as, for example, the sliding element, are not illustrated in FIG. 8A.

As is apparent in FIG. 8B, the ejection spring holding element 8 has an outer extension 8a which is in the form of a pin and, upon rotation of the sliding element 2, comes into contact with a corresponding guide surface 2a of the sliding element 2 such that rotation of the ejection spring holding element 8 takes place as described previously.

Figure 9:
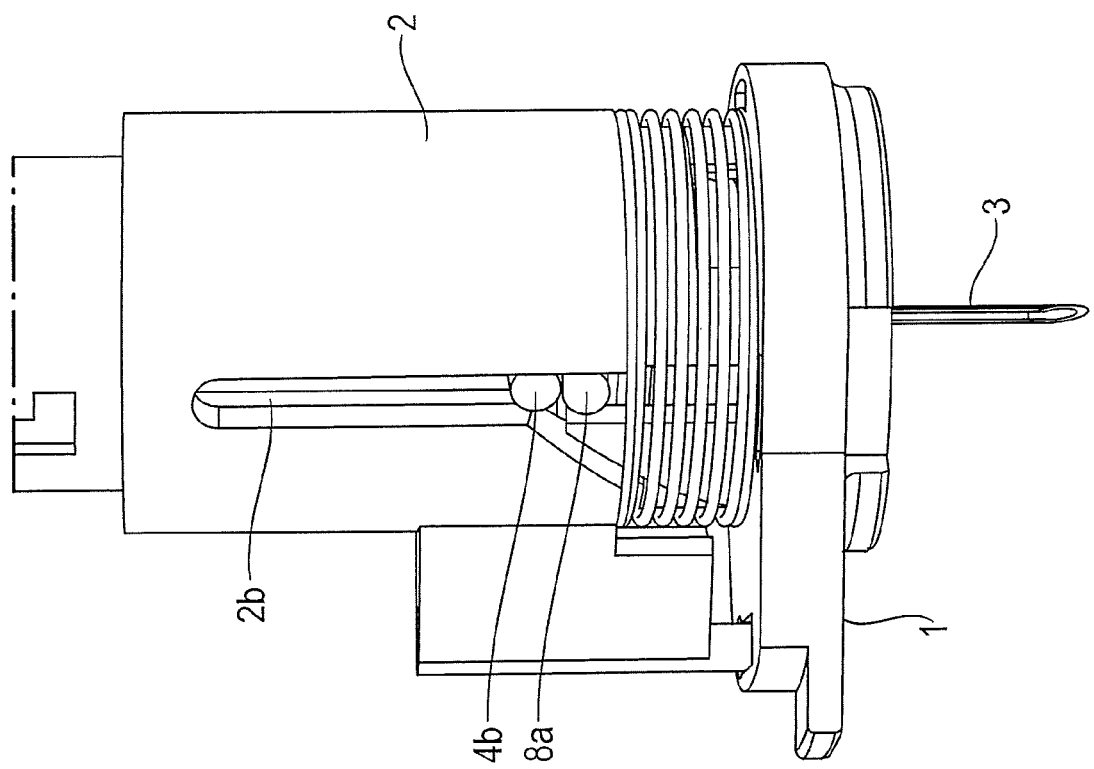
FIG. 9 shows a detailed view of the injector in the proximal end region of the injection operation.

FIG. 9 shows the state with the sliding element 2 completely pressed downward, and therefore the rotation of the sliding element 2 relative to the base element 1 is also finished. As is apparent, in said end state of the injection operation, both the outer pin 8a of the ejection spring holding element 8 and the extension 4b of the cannula upper part 4 are located in the region of a guide slot 2b of the sliding element 2. On the opposite side (not apparent), the extension 4c of the cannula upper part 4 is correspondingly located in a radially oppositely arranged guide slot of the sliding element 2.

In this state, there is therefore no limit for the extensions 4b and 4c and for the outer pin 8a in respect of a movement counter to the injection direction. As a result, an expansion of the ejection spring 7 takes place, and therefore ejection spring holding element 8 and cannula upper part 4 are pressed upward in an ejection operation counter to the injection direction. The holding element 5, by contrast, does not change the position because of the latched holding elements.

The cannula 3 is therefore pulled out of the patient's tissue, with the sensor 6 being prevented by the cam 5a of the holding element 5 from being pulled out.

Figure 11:
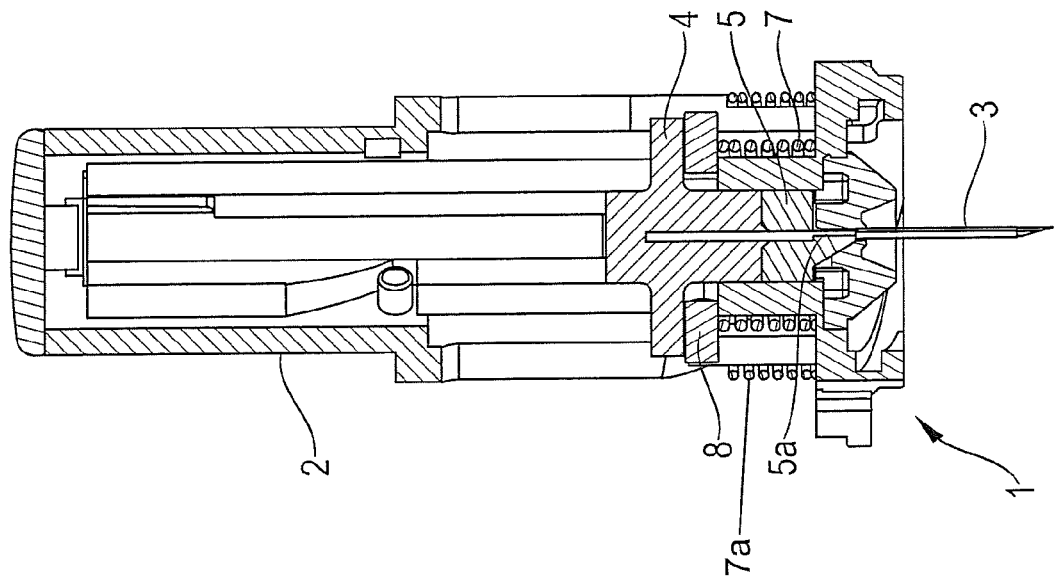
FIG. 11 shows a sectional illustration of the view according to FIG. 9.

FIG. 11 illustrates the configuration from FIG. 9 as a sectional image, wherein the injection axis lies within the sectional plane and the section runs along the intercepting line B according to FIG. 3. In particular the compressed ejection spring 7 is apparent here, said ejection spring acting firstly on the holding element 8 and secondly on the base element 1. A counterforce spring 7a is arranged concentrically with respect to the ejection spring 7, but with a greater radius, said counterforce spring firstly reacting on the base element 1 and secondly on the sliding element 2. Said counterforce spring is also completely compressed in this configuration. The counterforce spring serves in particular for the purpose of avoiding dropping down of the sliding element 2 because of gravitational force and for providing the user with an approximately constant counterforce during the injection operation in order to permit a uniform injection, in particular a uniform speed of penetration of the cannula 3 into the patient.

Figure 10:
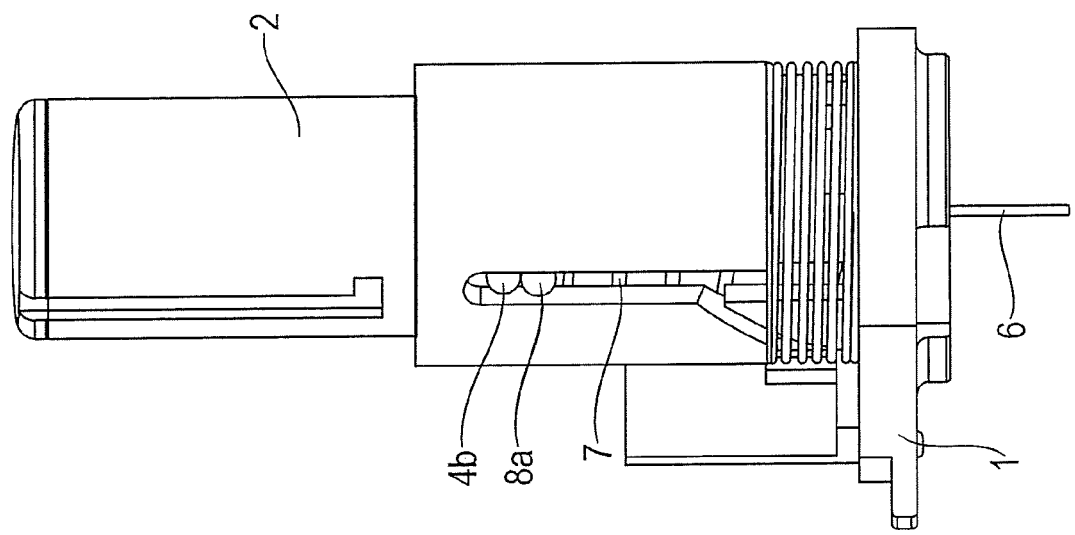
FIG. 10 shows a side view of the injector after the ejection operation is finished.

FIG. 10 illustrates the view according to FIG. 9, but after the ejection operation has finished.

As previously described, at the end of the injection operation the holding element 8 is rotated about the injection axis, and therefore it is transferred from a fixing position in which no movement of the holding element in the ejection direction, i.e. counter to the injection direction I, is possible, into an ejection position in which a movement can take place in the ejection direction.

As already described with respect to FIG. 8A, the holding element 8 has, on the inner side, a pin which, according to the fixing position illustrated in FIG. 8A, is arranged in a horizontally running slot of the base element 1, and therefore no movement in the ejection direction (upward in FIG. 8A) is possible.

At the end of the injection operation, the holding element 8 is rotated about the injection axis, in the clockwise direction according to FIG. 8A, and therefore the inner pin of the holding element 8 comes to lie in alignment with the guide slot 1a of the base element 1. By this means, a movement of the guide element 8 in the ejection direction (upward) is therefore possible. This rotation of the holding element 8 takes place since, at the end of the injection operation, because of the bevels 1d and 1c of the base element 1 and the corresponding bevels of the sliding element 2, rotation of the sliding element about the injection axis (in the present case in the clockwise direction) takes place and, by the surface 2a of the sliding element 2 that acts on the outer pin of the holding element 8, the rotation is transmitted to the holding element 8.

If the holding element 8 is in an ejection position, expansion of the expansion spring 7 is possible by this action, the holding element 8 is pressed upward and this movement is transmitted to the cannula upper part 4 and therefore also to the cannula 3, and therefore the cannula 3 is pulled out of the patient in an ejection operation. Due to the previously described holding element 5, the sensor 6, however, remains transcutaneously in the patient.

FIG. 10 now shows the situation after the ejection operation is finished: the ejection spring 7 is in an expanded state, holding element 8 and cannula upper part 4 (and also cannula 3) are pushed upward and located within the base element 1. However, the position of the sliding element 2 is unchanged, and therefore, as before, the outer counterforce spring is in a compressed state.

Figure 12:
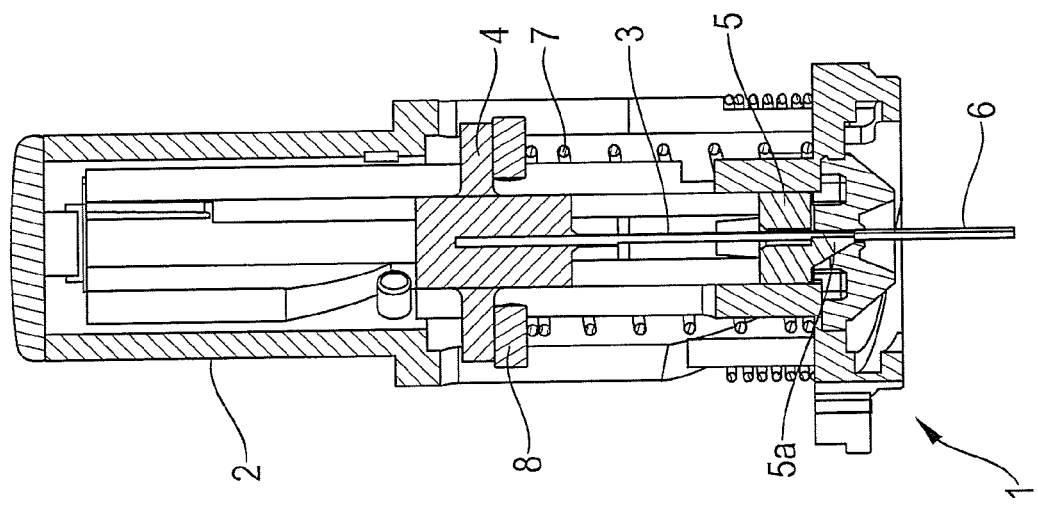
FIG. 12 shows a sectional illustration of the view according to FIG. 10.

FIG. 12 illustrates a section analogously to FIG. 11, but at the end of the ejection operation according to FIG. 10.

The injector according to the present exemplary embodiment furthermore has a cannula guide 9 for the cannula 3, as is apparent in particular in FIGS. 5 and 6.

The cannula guide 9 serves to guide the cannula in particular during the injection operation, but also during the ejection operation, in order to avoid tilting or lateral slippage. For this purpose, the cannula guide 9 is arranged on two opposite sides on the base element 1 and centrally has an elastic guide surface with an opening which is penetrated by the cannula 3 and divides the cannula guide 9 into two halves. FIG. 5 illustrates the state before the beginning of the injection. The cannula 3 is guided here in a proximal region by the cannula guide 9, and therefore, during the subsequent injection, tilting or lateral displacement is avoided.

After the injection operation is finished, the holding element 5 and the cannula upper part 4 reach the region of the cannula guide 9. Due to the division of the cannula guide 9 into two, the elastic elements of the cannula guide 9 can be pushed to the right and left by the holding element 5. This is the case in FIG. 6.

The invention claimed is:

1. An injector for transcutaneously introducing a sensor into a patient, the injector comprising:
   a cannula,
   a base element,
   a sliding element arranged displaceably on the base element, adapted for transcutaneously introducing the cannula into the patient in an injection direction in an injection operation, an ejection element configured to automatically pull the cannula out of the patient counter to the injection direction in an ejection operation, a locking element for the ejection element that, in a delivery state, locks the ejection element in an energy-charged state to hold energy until a start of the ejection operation, wherein the sliding element and the locking element are configured to interact indirectly or directly with one another such that, in an injection state in which the cannula is adapted to be introduced transcutaneously into the patient, the locking element for the ejection element is configured to release in order to automatically start the ejection operation, the locking element is configured to be fixable on the base element in a fixing position, and is configured to be displaceable on the base element counter to the injection direction in an ejection position to start the ejection operation, the locking element is arranged on the base element so as to be rotatable, and is configured to be transferable from the fixing position into the ejection position by rotation of the locking element, and at least one of the base element or the sliding element have at least one bevel which is arranged such that, during the injection operation, the sliding element rotates relative to the base element as the sliding element is displaced in the injection direction, and the relative rotation takes place only upon the sliding element reaching a proximal end region adjacent to the base element in which the cannula is completely introduced.

2. The injector according to claim 1, wherein the cannula is arranged in a distal end region on a cannula upper part of the injector, the cannula upper part is arranged on the base element so as to be displaceable in the injection direction, and the ejection element is configured to interact with the cannula upper part such that the cannula upper part is displaceable counter to the injection direction by the ejection element.

3. The injector according to claim 2, wherein the cannula upper part has a central element on which the cannula is arranged and has at least one guide extension, and the base element has at least one guide wall with a guide slot for the guide extension of the cannula upper part, configured for guiding the cannula upper part in the injection direction.

4. The injector according to claim 3, wherein the guide extension penetrates the guide wall of the base element, and the sliding element is configured to engage on the guide extension.

5. The injector according to claim 1, wherein the locking element is arranged between the ejection element and the cannula upper part such that a force is transmittable in the ejection direction to the cannula upper part via the locking element by the ejection element.

6. The injector according to claim 1, wherein the ejection element comprises an ejection spring.

7. The injector according to claim 6, wherein the ejection spring is securable in a tensioned or compressed state by the locking element.

8. The injector according to claim 1, wherein the sliding element and the locking element have corresponding contact surfaces which are arranged such that, by rotation of the sliding element, the ejection element is released from the fixing position.

9. The injector according to claim 8, wherein the locking element has an extension and the sliding element has a corresponding guide surface.

10. The injector according to claim 1, wherein the base element and the sliding element have corresponding guide elements which are configured such that the sliding element is rotatable relative to the base element only upon the sliding element reaching the proximal end region.

11. The injector according to claim 10, wherein the cannula is arranged in a distal end region on a cannula upper part of the injector, and the cannula upper part is displaceable on the base element in the injection direction, the ejection element is configured to interact with the cannula upper part such that the cannula upper part is displaceable counter to the injection direction by the ejection element, and the sliding element has guide slots for the guide extension of the cannula upper part, said guide slots being arranged in such a manner that, after rotation of the sliding element in the proximal end region, the cannula upper part is displaceable counter to the injection direction.

12. The injector according to claim 11, wherein the bevel is formed on the sliding element at a proximal end of the guide slots.

13. The injector according to claim 1, further comprising a counterforce spring arranged between the base element and the sliding element that acts counter to a displacement of the sliding element in the injection direction.

* * * * *